(12) United States Patent
Takahashi

(10) Patent No.: US 9,060,706 B2
(45) Date of Patent: Jun. 23, 2015

(54) CAPSULE MEDICAL DEVICE

(71) Applicant: OLYMPUS MEDICAL SYSTEMS CORP., Tokyo (JP)

(72) Inventor: Masaki Takahashi, Saitama (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 52 days.

(21) Appl. No.: 14/083,677

(22) Filed: Nov. 19, 2013

(65) Prior Publication Data

US 2014/0142380 A1    May 22, 2014

Related U.S. Application Data

(63) Continuation of application No. PCT/JP2013/065448, filed on Jun. 4, 2013.

(30) Foreign Application Priority Data

Jun. 8, 2012    (JP) .................................. 2012-131254

(51) Int. Cl.
    *A61B 1/04*        (2006.01)
    *A61B 1/06*        (2006.01)
    (Continued)

(52) U.S. Cl.
    CPC .............. *A61B 1/06* (2013.01); *A61B 1/00032* (2013.01); *A61B 1/041* (2013.01); *A61B 1/00016* (2013.01); *A61B 1/0011* (2013.01)

(58) Field of Classification Search
    CPC .............. A61B 1/041; A61B 1/00025; A61B 1/00027; A61B 1/00036; A61B 1/00105

USPC ......... 600/109, 130, 160; 606/32; 429/97, 98, 429/99, 100, 157, 158

See application file for complete search history.

(56) References Cited

U.S. PATENT DOCUMENTS

| 7,647,090 B1 * | 1/2010 | Frisch et al. ................... 600/473 |
| 8,177,712 B2 * | 5/2012 | Fujimori et al. ............... 600/176 |

(Continued)

FOREIGN PATENT DOCUMENTS

| JP | 2004-65772 A | 3/2004 |
| JP | 2007-185522 A | 7/2007 |

(Continued)

OTHER PUBLICATIONS

International Search Report dated Aug. 13, 2013 from related International Application No. PCT/JP2013/065448.

(Continued)

*Primary Examiner* — Thomas J Sweet
*Assistant Examiner* — William Chou
(74) *Attorney, Agent, or Firm* — Scully, Scott, Murphy & Presser, PC

(57) ABSTRACT

A capsule medical device includes: a casing having a capsule shape; a plurality of batteries, each having a first face, a second face, a first electrode and a second electrode; and a short-circuit prevention member, wherein the short-circuit prevention member includes an insulating member having an annular shape, covering the portion of the second electrode, and formed with an aperture from which the first electrode is exposed, an outer diameter of the annular shape is smaller than an inner diameter of the casing, and larger than an outer diameter of the battery, and a diameter of the aperture is larger than a diameter of the first electrode, and smaller than a diameter of the portion of the second electrode.

6 Claims, 17 Drawing Sheets

(51) Int. Cl.
 *H01M 6/42* (2006.01)
 *A61B 1/00* (2006.01)

(56) References Cited

U.S. PATENT DOCUMENTS

2006/0241578 A1* 10/2006 Honda .............................. 606/32
2007/0072065 A1* 3/2007 Saugier et al. .................. 429/97
2012/0002349 A1* 1/2012 Ito et al. ......................... 361/502
2012/0296165 A1 11/2012 Segawa
2013/0231532 A1* 9/2013 Makino ......................... 600/109

FOREIGN PATENT DOCUMENTS

| JP | 2007-307005 A | 11/2007 |
| JP | 2009-61282 A | 3/2009 |
| JP | 2012-104441 A | 5/2012 |
| WO | 2012/073634 A1 | 6/2012 |

OTHER PUBLICATIONS

Notice of Rejection dated Jan. 21, 2014 from related Japanese Application No. 2013-552025, together with a partial English language translation.

* cited by examiner

FIG.15A
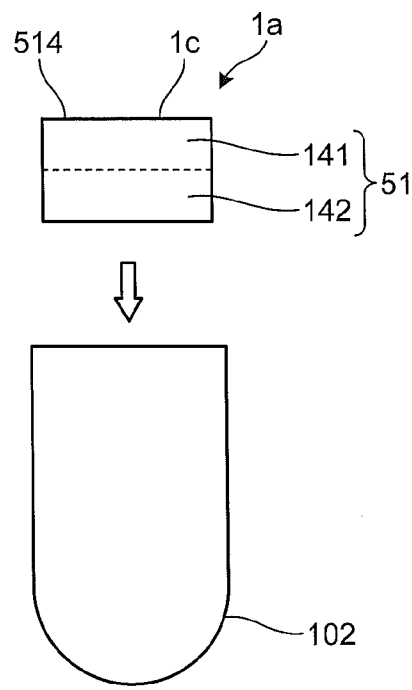
FIG.15B
FIG.15C
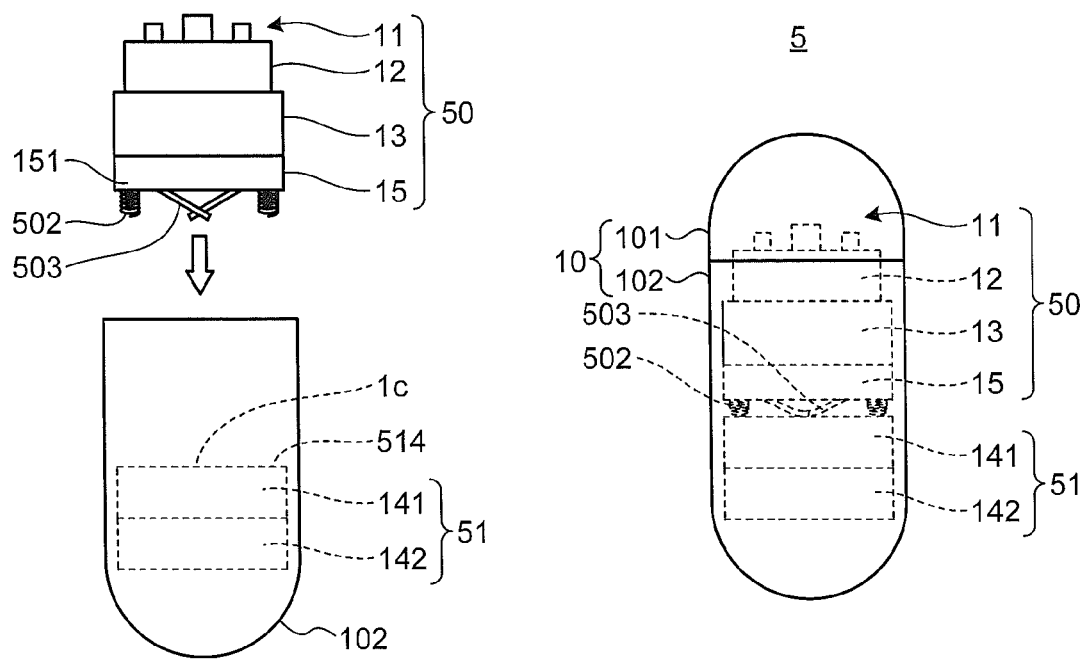

CAPSULE MEDICAL DEVICE

CROSS-REFERENCE TO RELATED APPLICATIONS

This application is a continuation of PCT international application Ser. No. PCT/JP2013/065448 filed on Jun. 4, 2013 which designates the United States, incorporated herein by reference, and which claims the benefit of priority from Japanese Patent Applications No. 2012-131254, filed on Jun. 8, 2012, incorporated herein by reference.

BACKGROUND OF THE INVENTION

1. Field of the Invention

The present invention relates to a capsule medical device that is introduced into a subject to capture an in-vivo image.

2. Description of the Related Art

Recently, in a field of an endoscope, a capsule medical device having an imaging function and a wireless communication function in a capsule-shaped casing has been developed. In general, a capsule medical device is introduced into a body of a subject to capture an inside of the body of the subject, thereby acquiring information relating to the subject, such as an image (e.g., see Japanese Laid-open Patent Publication No. 2004-65772).

A compact device such as a capsule medical device generally uses a button battery as a battery for supplying power supply to various devices such as an imaging device or a wireless module. A button battery has a disk-like shape (button shape) with two opposing surfaces as a whole. A negative electrode is provided on one surface (negative-electrode surface) of the button shape, while a positive electrode covers a peripheral edge of the negative-electrode surface from the other surface through a side face. Conventionally, a capsule medical device described above is assembled in such a manner that plural substrates on which various devices are mounted and plural button batteries are sequentially inserted into a capsule-shaped casing.

SUMMARY OF THE INVENTION

A capsule medical device according to one aspect of the present invention includes: a casing having a capsule shape; a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein the short-circuit prevention member includes an insulating member having an annular shape, covering the portion of the second electrode, and formed with an aperture from which the first electrode is exposed, an outer diameter of the annular shape is smaller than an inner diameter of the casing, and larger than an outer diameter of the battery, and a diameter of the aperture is larger than a diameter of the first electrode, and smaller than a diameter of the portion of the second electrode.

A capsule medical device according to another aspect of the present invention includes: a casing having a capsule shape; a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein the short-circuit prevention member includes: an insulating member having a disk-like shape, an electrode pad provided on one surface of the insulating member and is in contact with at least a part of the first electrode, a contact member that is provided on the other surface of the insulating member, and is in contact with the second face, and a conductive unit that is provided in the insulating member for electrically connecting the electrode pad and the contact member.

A capsule medical device according to still another aspect of the present invention includes: a casing having a capsule shape; a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein the short-circuit prevention member includes a contact member including a plane portion, and a spring portion standing from the plane portion toward one side in an oblique direction with respect to a major surface of the plane portion, and an insulating member that has an annular shape formed with an aperture on its central part, and that covers a peripheral edge of a major surface on one side of the plane portion, and a diameter of the aperture is smaller than an inner diameter of the portion of the second electrode.

A capsule medical device according to yet another aspect of the present invention includes: a casing having a capsule shape; a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein the short-circuit prevention member includes a contact member including a plane portion, and at least two spring portions standing from the plane portion toward both sides, respectively, in an oblique direction with respect to a major surface of the plane portion, and an insulating member that has an annular shape formed with an aperture on its central part, and that covers a peripheral edge of a major surface on both sides of the plane portion.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 33 is a side view illustrating the battery illustrated in FIG. 1;

FIG. 15A is a view for describing a method of manufacturing the capsule medical device illustrated in FIG. 13;

FIG. 15B is a view for describing the method of manufacturing the capsule medical device illustrated in FIG. 13;

FIG. 15C is a view for describing the method of manufacturing the capsule medical device illustrated in FIG. 13;

DETAILED DESCRIPTION OF THE PREFERRED EMBODIMENTS

Figure 1:
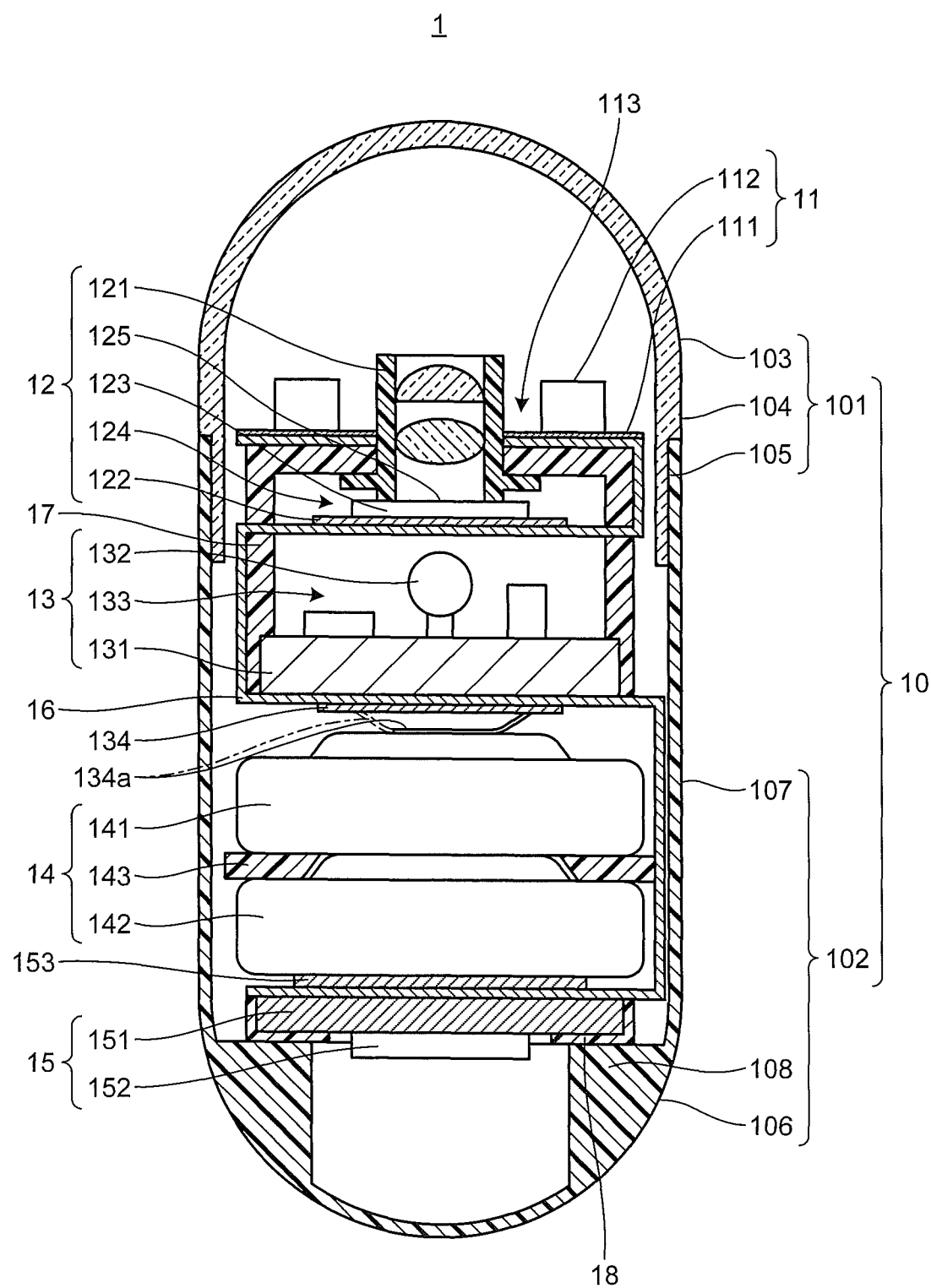
FIG. 1 is a sectional view illustrating an example of a configuration of a capsule medical device according to a first embodiment of the present invention.

A capsule medical device according to the embodiments of the present invention will be described below with reference to the drawings. The present invention is not limited to these embodiments. The same components are identified by the same reference numerals in each drawing. In addition, it should be noted that the drawings are schematic and ratios of dimensions and the like are different from actual ones. Therefore, the drawings also include portions having different dimensional relationships and ratios from each other.

First Embodiment

FIG. 1 is a sectional view illustrating a configuration of a capsule medical device according to a first embodiment of the present invention. As illustrated in FIG. 1, a capsule medical device 1 includes a capsule-shaped casing 10 having a dome portion 101 with a hemispherical shape and a bottomed case portion 102 with a cylindrical portion, an illumination unit 11 housed in the casing 10, an imaging unit 12, a control unit 13, a battery unit 14, a wireless communication unit 15, and a flexible substrate 16 that electrically connects the illumination unit 11, the imaging unit 12, the control unit 13, and the wireless communication unit 15, wherein the illumination unit 11, the imaging unit 12, the control unit 13, and the wireless communication unit 15 are function execution sections out of these units, and are mounted on the flexible substrate 16. Out of these units, the illumination unit 11, the imaging unit 12, and the control unit 13 are assembled on a spacer 17 to be formed as a unit, the spacer 17 being made of a resin material. The wireless communication unit 15 is assembled on a spacer 18 to be formed as a unit, the spacer 18 being made of a resin material.

The dome portion 101 includes a dome hemispherical portion 103 having a hemispherical shape and serving as one end of the capsule medical device 1 in the longitudinal direction, a dome holding portion 104 in a cylindrical shape having an outer diameter equal to the outer diameter of the dome hemispherical portion 103, and a dome cylindrical portion 105 that is formed with a cutout for making the outer diameter smaller than that of the dome holding portion 104 and is fitted to the case portion 102. The dome portion 101 described above is made of a material (e.g., a resin material such as polycarbonate, acryl, or cycloolefin polymer) that is transparent for illumination light, such as visible light, emitted from the illumination unit 11, and has biocompatibility.

The case portion 102 includes a case hemispherical portion 106 having a hemispherical shape; and a case cylindrical portion 107 having a cylindrical shape, having an outer diameter equal to the outer diameter of the case hemispherical portion 106 and coupled to the case hemispherical portion 106. The case hemispherical portion 106 becomes the other end of the capsule medical device 1 in the longitudinal direction. A case inner-wall rib 108 projecting toward the inner periphery is formed on plural portions on the inside of the case hemispherical portion 106 in order to position each component housed in the casing 10. The case portion 102 may be opaque and colored, and is made of a material (e.g., a resin material such as polysulfone or polycarbonate) having biocompatibility.

The dome portion 101 and the case portion 102 are bonded watertight to each other by an adhesive (not illustrated) applied between the outer periphery of the dome cylindrical portion 105 and the inner periphery on the end of the case cylindrical portion 107.

The illumination unit 11 includes a flexible illumination substrate 111 formed integral with the flexible substrate 16, and plural illumination devices 112 arranged on the illumination substrate 111. The illumination device 112 is an LED that generates white illumination light, and is arranged around an aperture 113 formed on almost the center of the illumination substrate. These illumination devices 112 are connected to a later-described illumination drive circuit.

The position of the illumination unit 11 in the casing 10 is determined by inserting a later-described lens unit 121 into the aperture 113 of the illumination substrate 111.

The imaging unit 12 includes a lens unit 121 having plural objective lenses mounted to a lens frame, a flexible imaging substrate 122 formed integral with the flexible substrate 16, an image sensor 123, such as CMOS, flip-chip mounted on the imaging substrate 122, and a circuit unit 124 that allows the image sensor 123 to execute an imaging operation. The image sensor 123 is arranged with a light-receiving surface 125 facing the lens unit 121, and it generates an electric signal indicating an image by photoelectrically converting received light passing through the lens unit 121. The circuit unit 124 controls the imaging operation by the image sensor 123, and includes various processing circuits that convert the electric signal generated by the image sensor 123 into an image signal after performing a predetermined signal process to the electric signal.

The control unit 13 includes a control substrate 131 made of a rigid substrate, a lead switch 132 mounted on the control substrate 131, and a group 133 of various electronic components. The control substrate 131 is electrically connected to the flexible substrate 16 with soldering. The lead switch 132 makes a switching operation in response to an external magnetic field. The electronic component group 133 includes, for example, a power supply IC that controls start/stop of a power supply according to the switching operation of the lead switch 132, a memory that stores operation setting information or other information, a crystal sound wave generator, a power supply control unit that controls a supply of electric power to the illumination unit 11 and the imaging unit 12, and an illumination drive unit that drives the illumination unit 11.

A negative-electrode contact portion 134 having spring property is mounted on the surface of the flexible substrate 16 on the back of the control substrate 131 (the lower side in FIG. 1) by using solder. The negative-electrode contact portion 134 is brought into contact with a negative electrode 1c of a battery 141, described later, to electrically connect the battery unit 14 and the flexible substrate 16.

Figure 2:
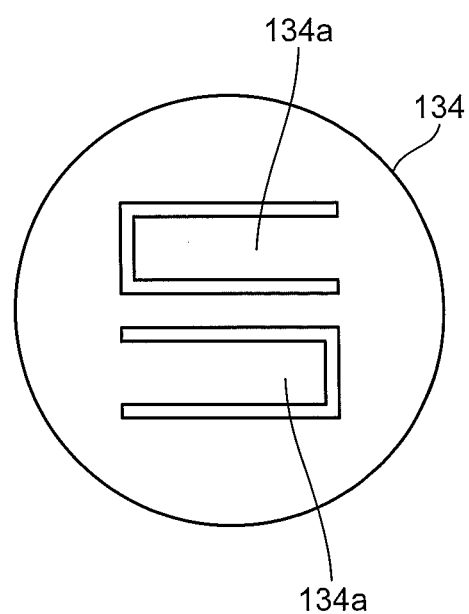
FIG. 2 is a top view illustrating a structure of a negative-electrode contact portion illustrated in FIG. 1.

FIG. 2 is a top view illustrating the negative-electrode contact portion 134. The negative-electrode contact portion 134 is elastically compressed when being housed in the casing 10, and includes one or more (two in FIG. 2) spring portions 134a that electrically connect the control substrate 131 and the battery 141. The negative-electrode contact portion 134 thus configured biases the components housed in the casing 10 in both directions across the negative-electrode contact portion 134 by absorbing tolerance in the casing 10.

The battery unit 14 includes a plurality (two in FIG. 1) of batteries 141 and 142 coaxially connected in series, and a short-circuit prevention member 143 arranged between the batteries 141 and 142. The battery unit 14 feeds electric power to each of the illumination unit 11, the imaging unit 12, the control unit 13, and the wireless communication unit 15.

Figure 3A:
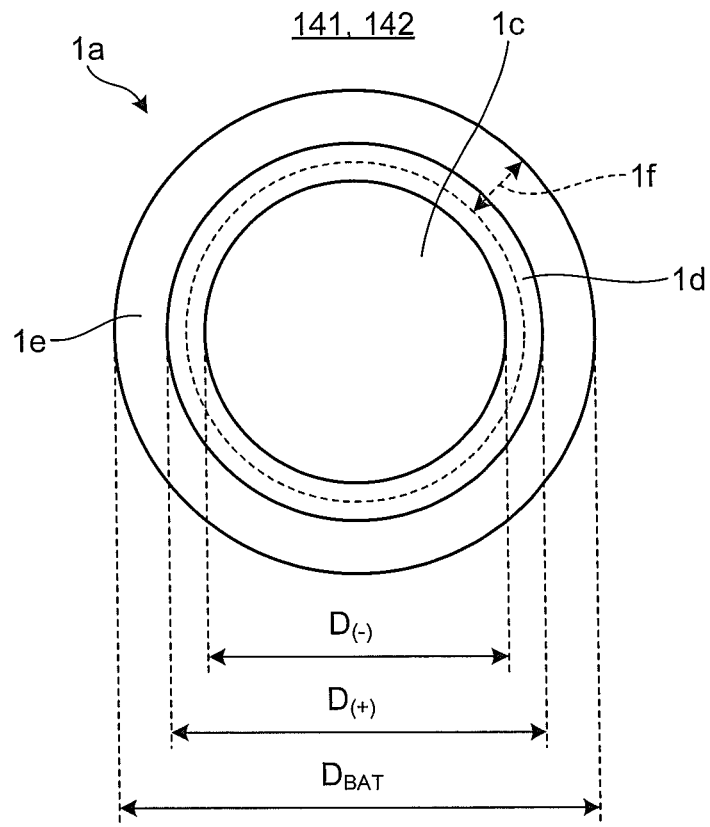
FIG. 3A is a top view of a battery illustrated in FIG. 1.
Figure 3B:
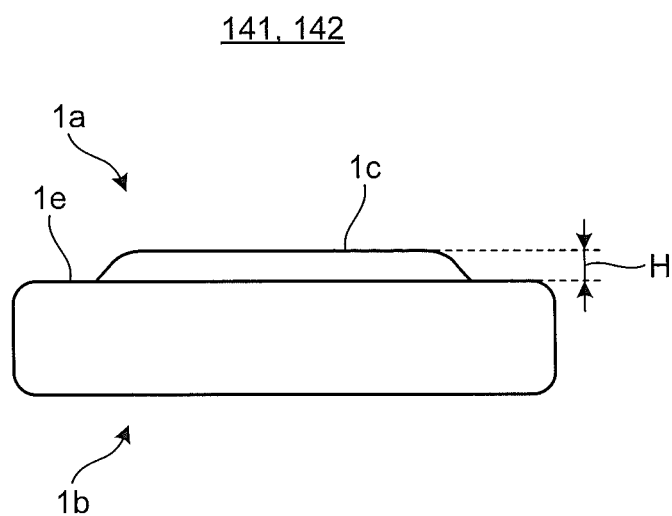

FIG. 3A is a top view illustrating the batteries 141 and 142, while FIG. 3B is a side view illustrating the same. As illustrated in FIGS. 3A and 3B, the batteries 141 and 142 are silver oxide batteries generally called button battery, and include opposite two surfaces, i.e., a negative-electrode surface 1a that is the top surface and a positive-electrode surface 1b that is the bottom surface in FIG. 3B. A negative electrode 1c is formed on the central region of the negative-electrode surface 1a so as to project from the negative-electrode surface 1a. On the other hand, a positive electrode is formed over the peripheral edge of the negative-electrode surface 1a through the side face from the positive-electrode surface 1b, thereby forming a so-called positive electrode can. In the positive electrode, the positive-electrode portion located on the peripheral edge of the negative-electrode surface 1a is referred to as a peripheral edge positive-electrode portion 1e below. On the negative-electrode surface 1a, the negative electrode 1c and the peripheral edge positive-electrode portion 1e are electrically insulated from each other by a separator 1d formed between both of them.

The short-circuit prevention member 143 prevents short-circuit between the negative electrode 1c and the peripheral edge positive-electrode portion 1e on the negative-electrode surface 1a of the battery 142, while keeping an electrical connection between the positive-electrode surface 1b of the battery 141 and the negative electrode 1c of the battery 142. The detailed structure of the short-circuit prevention member 143 will be described later.

The wireless communication unit 15 includes a wireless communication substrate (wireless substrate) 151, and an electronic component 152 for wireless communication mounted on the wireless substrate 151. The wireless substrate 151 is made of a rigid substrate, and is electrically connected to the flexible substrate 16 by using solder. The wireless substrate 151 is also formed with an antenna (not illustrated) for transmitting a wireless signal. The wireless communication unit 15 wirelessly transmits an image signal generated by the imaging unit 12 from the antenna.

An electrode pad (land) 153 is formed on the surface of the flexible substrate 16 at the back of the wireless substrate 151 (on the upper side in FIG. 1). The electrode pad 153 is brought into contact with the positive electrode of the battery 142 to electrically connect the battery unit 14 and the flexible substrate 16.

The capsule medical device 1 thus configured is introduced into a subject for capturing the inside of the subject, and wirelessly transmits an image signal acquired by the imaging process to the outside of the subject. A receiving device that receives the wireless signal transmitted from the capsule medical device 1 is provided on the outside of the subject. A predetermined signal process is executed to the wireless signal (image signal) received by the receiving device, whereby an image indicating the inside of the subject is generated.

Figure 4A:
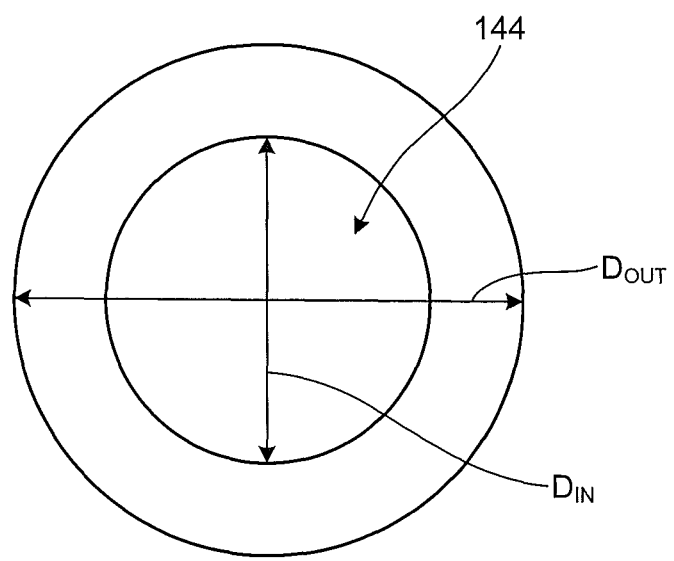
FIG. 4A is a top view illustrating a short-circuit prevention member illustrated in FIG. 1.
Figure 4B:
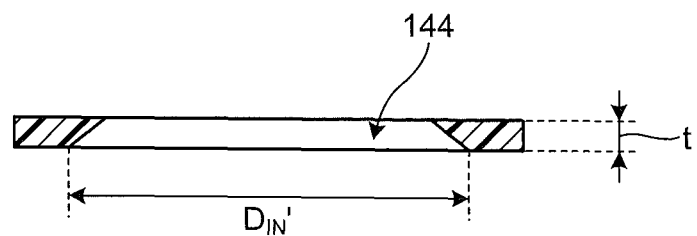
FIG. 4B is a sectional view illustrating the short-circuit prevention member illustrated in FIG. 4A.

The detailed structure of the short-circuit prevention member 143 will next be described. FIG. 4A is a top view illustrating the short-circuit prevention member 143, and FIG. 4B is a sectional side view illustrating the same. The short-circuit prevention member 143 is made of an insulating material such as resin. Preferably, the short-circuit prevention member 143 may be made of a grippy material (a material that can easily stop the movement of the batteries 141 and 142 by friction force), such as silicon or sponge, in order to prevent the relative positional deviation between the batteries 141 and 142, when the short-circuit prevention member 143 is arranged between the batteries 141 and 142.

As illustrated in FIG. 4A, the short-circuit prevention member 143 has an annular shape formed with an aperture 144 on its inside. An outer diameter $D_{OUT}$ of the short-circuit prevention member 143 is smaller than an inner diameter of the casing 10, and preferably larger than an outer diameter $D_{BAT}$ (see FIG. 3A) of the batteries 141 and 142. On the other hand, an inner diameter $D_{IN}$ of the short-circuit prevention member 143 is larger than an outer diameter $D_{(-)}$ of the negative electrode 1c of the batteries 141 and 142 (i.e., the inner diameter of the separator 1d), and smaller than the inner diameter (i.e., the outer diameter of the separator 1d) $D_{(+)}$ of the peripheral edge positive-electrode portion 1e. Since the size of the short-circuit prevention member 143 is specified as described above, the negative electrode 1c is exposed from the aperture 144, and the region (insulating target region 1f) slightly inward of the inner diameter of the peripheral edge positive-electrode portion 1e from the outer periphery of the battery 142 is covered by the short-circuit prevention member 143, when the short-circuit prevention member 143 is arranged on the negative-electrode surface 1a of the battery 142.

When the edge of the negative electrode 1c of the batteries 141 and 142 are tapered to become wider toward the bottom as illustrated in FIG. 3B, the cross-section of the aperture 144 orthogonal to the aperture face may be tapered according to the tapered edge (see FIG. 4B). In this case, the diameter $D_{IN}'$ of the wider part (lower side in the figure) of the aperture may be smaller than the inner diameter $D_{(+)}$ of the peripheral edge positive-electrode portion 1e. With this structure, the exposure of the peripheral edge positive-electrode portion 1e can surely be prevented.

The thickness t of the short-circuit prevention member 143 may be smaller than the height H (see FIG. 3B) of the negative electrode 1c projecting from the negative-electrode surface 1a. With this structure, the short-circuit prevention member 143 allows the negative electrode 1c to project from the aperture 144, when the short-circuit prevention member 143 is put on the battery 142, whereby the electrical connection between the negative electrode 1c and the positive-electrode surface 1b of the battery 141 can be secured.

When the short-circuit prevention member 143 is made of an expandable material such as a sponge, the thickness t before the short-circuit prevention member 143 is arranged may be larger than the height H of the negative electrode 1c, if the thickness t of the short-circuit prevention member 143 can be compressed to be smaller than the height H of the negative electrode 1c when the short-circuit prevention member 143 is arranged between the batteries 141 and 142.

Figure 5A:
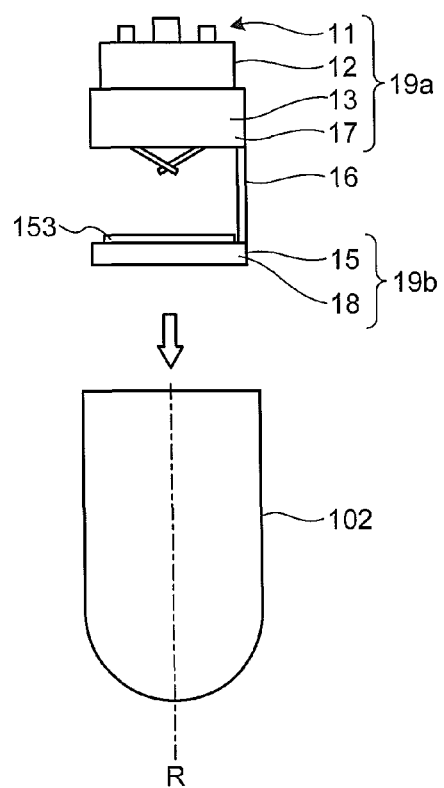
FIG. 5A is a view for describing a method of manufacturing the capsule medical device illustrated in FIG. 1.

Subsequently, a method of manufacturing the capsule medical device 1 will be described with reference to FIGS. 5A to 5F. Firstly, as illustrated in FIG. 5A, the illumination unit 11, the imaging unit 12, and the control unit 13 out of the function sections housed in the casing 10 are mounted on the spacer 17 beforehand to form a first unit 19a. On the other hand, the wireless communication unit 15 connected to the control unit 13 via the flexible substrate 16 is mounted on the spacer 18 to form a second unit 19b. The case portion 102 is arranged with a long axis R being defined as the vertical direction and with the aperture facing upward, and the second unit 19b is inserted into the case portion 102 with the electrode pad 153 formed on the wireless communication substrate 151 facing upward.

Figure 5B:
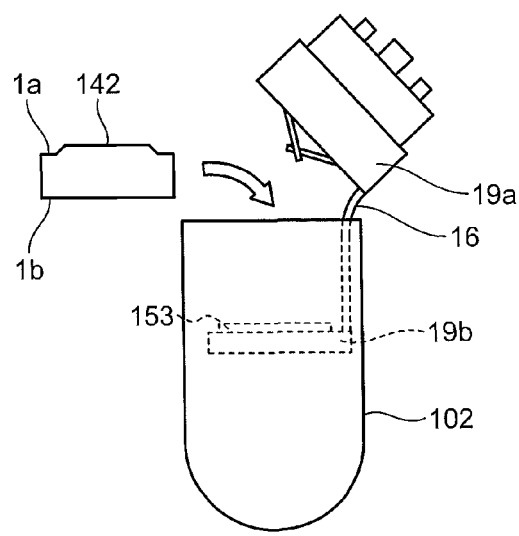
FIG. 5B is a view for describing the method of manufacturing the capsule medical device illustrated in FIG. 1.
Figure 5C:
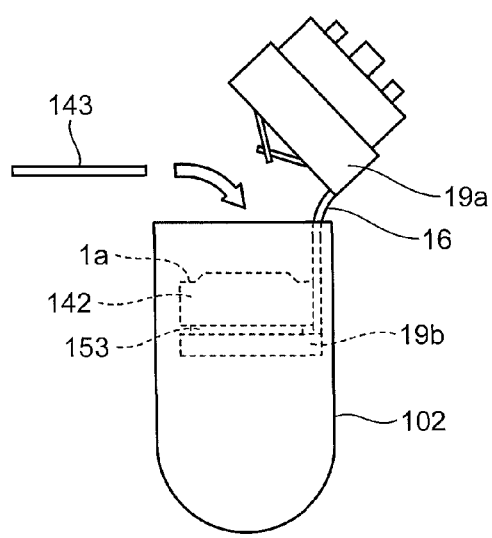
FIG. 5C is a view for describing the method of manufacturing the capsule medical device illustrated in FIG. 1.

As illustrated in FIG. 5B, after the second unit 19b is inserted into the case portion 102, the battery 142 is inserted such that the positive-electrode surface 1b faces downward. Then, as illustrated in FIG. 5C, the short-circuit prevention member 143 is arranged on the negative-electrode surface 1a of the battery 142.

Figure 5D:
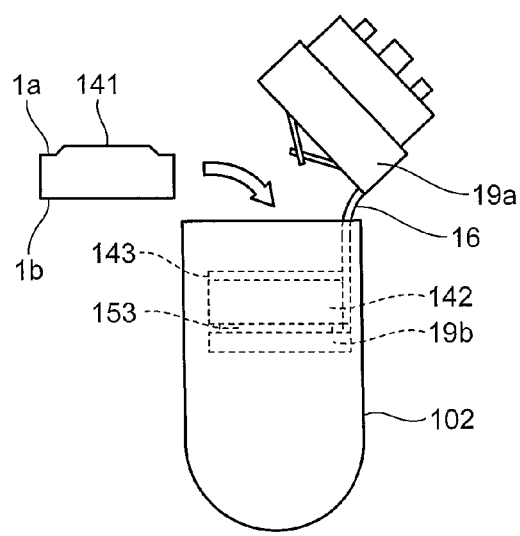
FIG. 5D is a view for describing the method of manufacturing the capsule medical device illustrated in FIG. 1.
Figure 5E:
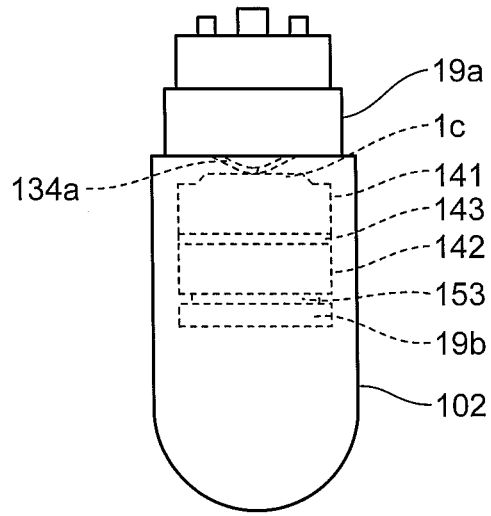
FIG. 5E is a view for describing the method of manufacturing the capsule medical device illustrated in FIG. 1.

Next, as illustrated in FIG. 5D, the battery 141 is inserted on the short-circuit prevention member 143 such that the positive-electrode surface 1b faces downward. Then, as illustrated in FIG. 5E, a spring portion 134a of the negative-electrode contact portion 134 formed on the first unit 19a is brought into contact with the negative electrode 1c of the battery 141, and with this state, the first unit 19a, the batteries 141 and 142 and the second unit 19b are put into the case portion 102.

Figure 5F:
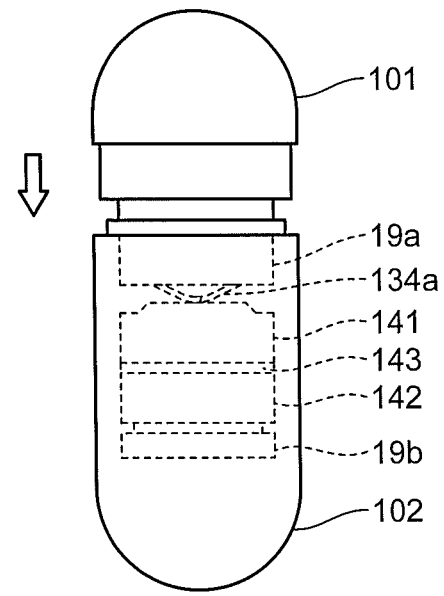
FIG. 5F is a view for describing the method of manufacturing the capsule medical device illustrated in FIG. 1.

As illustrated in FIG. 5F, the dome portion 101 is put on the case portion 102, and they are bonded by using an adhesive to seal the casing 10. In this case, the adhesive can be cured, while applying load in the longitudinal direction of the casing 10 in order to prevent the dome portion 101 from floating from the case portion 102 due to the spring property of the negative-electrode contact portion 134. Thus, the capsule medical device 1 illustrated in FIG. 1 is completed.

As described above, according to the first embodiment, the annular short-circuit prevention member 143 is arranged between the battery 141 and the battery 142, whereby the short-circuit on the negative-electrode surface 1a of the battery 142 can be prevented, while securing the electrical connection between the battery 141 and the battery 142.

Modification 1-1

Subsequently, Modification 1-1 of the first embodiment will be described.

In the first embodiment, the short-circuit prevention member 143 that can be attached to and detached from the batteries 141 and 142 is provided to prevent the short-circuit on the negative-electrode surface 1a of the battery 142. However, the short-circuit prevention member may directly be fixed to the battery 142.

For example, a short-circuit prevention member having an annular shape similar to the one illustrated in FIG. 3A and having a seal type adhesive member with adhesive property applied on one surface may be applied on the insulating target region 1f on the negative-electrode surface 1a of the battery 142.

Alternatively, a short-circuit prevention member may be formed by directly applying a coating material having insulation property such as an adhesive on the insulating target region 1f, and curing this coating material. In this case, if a material with a friction coefficient relatively higher than that on the cured surface (e.g., a friction coefficient higher than that of a metal on the surface of the batteries 141 and 142) is used for the coating material, the movement of the batteries 141 and 142 can be stopped by the friction force to prevent the positional deviation. Therefore, this structure is preferable.

Modification 1-2

Subsequently, Modification 1-2 of the first embodiment will be described.

Figure 6:
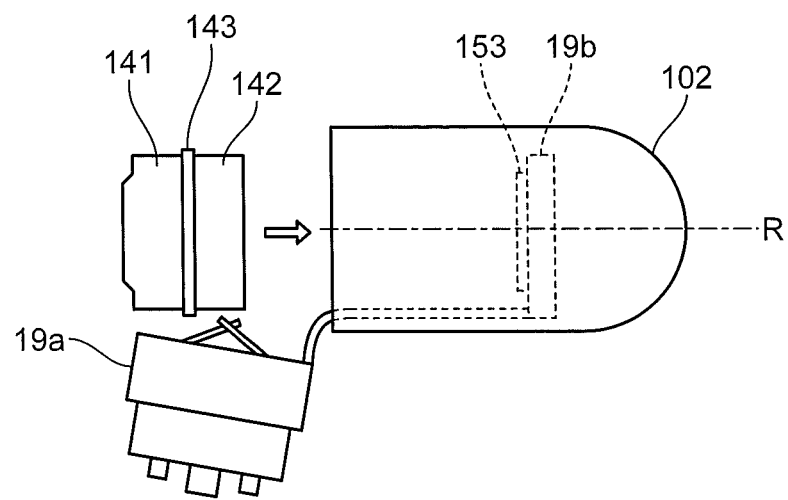
FIG. 6 is a view for describing another method of manufacturing the capsule medical device illustrated in FIG. 1.

In the first embodiment, the capsule medical device is assembled such that the long axis R of the case portion 102 is along the vertical direction. However, the capsule medical device can be assembled such that the long axis R of the case portion 102 is along the horizontal direction. In this case, as illustrated in FIG. 6, the second unit 19b is firstly inserted into the case portion 102 whose long axis R is along the horizontal direction. On the other hand, the battery 141 and the battery 142 are held with the short-circuit prevention member 143 being interposed between them on the outside of the case portion 102. In this case, if an adhesive is applied on both surfaces of the short-circuit prevention member 143, it becomes easy to hold the battery 141 and the battery 142 with the short-circuit prevention member 143 being interposed between them. The battery 141, the short-circuit prevention member 143, and the battery 142, which keeps the state described above, are pushed into the case portion 102 from the positive-electrode surface 1b of the battery 142. Then, the first unit 19a is pushed into the case portion 102, the dome portion 101 is put on the case portion 102, and they are fixed by an adhesive (see FIG. 5F).

As described above, even in the case where the capsule medical device 1 is assembled with the case portion 102 directing the horizontal direction, the short-circuit of the battery 142 can surely be prevented by the formation of the short-circuit prevention member 143 between the battery 141 and the battery 142.

Second Embodiment

Subsequently, a second embodiment of the present invention will be described.

Figure 7:
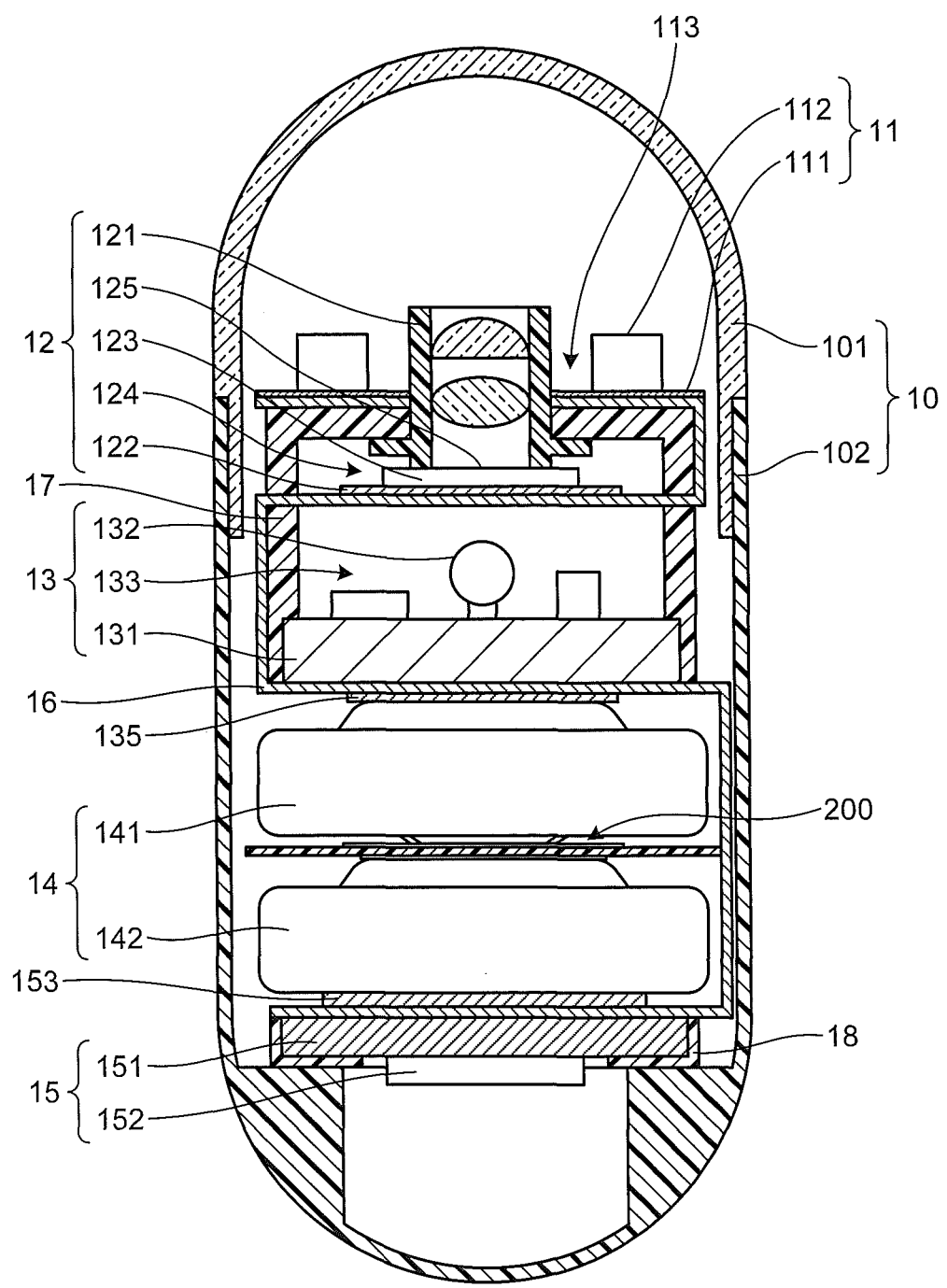
FIG. 7 is a sectional view illustrating an example of a configuration of a capsule medical device according to a second embodiment of the present invention.

FIG. 7 is a sectional view illustrating a configuration of a capsule medical device according to the second embodiment of the present invention. As illustrated in FIG. 7, a capsule medical device 2 according to the second embodiment includes an electrode pad 135 instead of the negative-electrode contact portion 134 illustrated in FIG. 1, and includes a short-circuit prevention member 200 instead of the short-circuit prevention member 143. The configuration of the capsule medical device 2 except for the electrode pad 135 and the short-circuit prevention member 200 is the same as that illustrated in FIG. 1.

The electrode pad 135 is a flat-type metal member formed on the surface of the flexible substrate 16 on the back of the control substrate 131, and it is electrically connected to the negative electrode 1c of the battery 141.

The short-circuit prevention member 200 is arranged between the battery 141 and the battery 142. It electrically connects the battery 141 and the battery 142, and prevents a short-circuit between the negative electrode 1c and the peripheral edge positive-electrode portion 1e on the negative-electrode surface 1a of the battery 142.

Figure 8A:
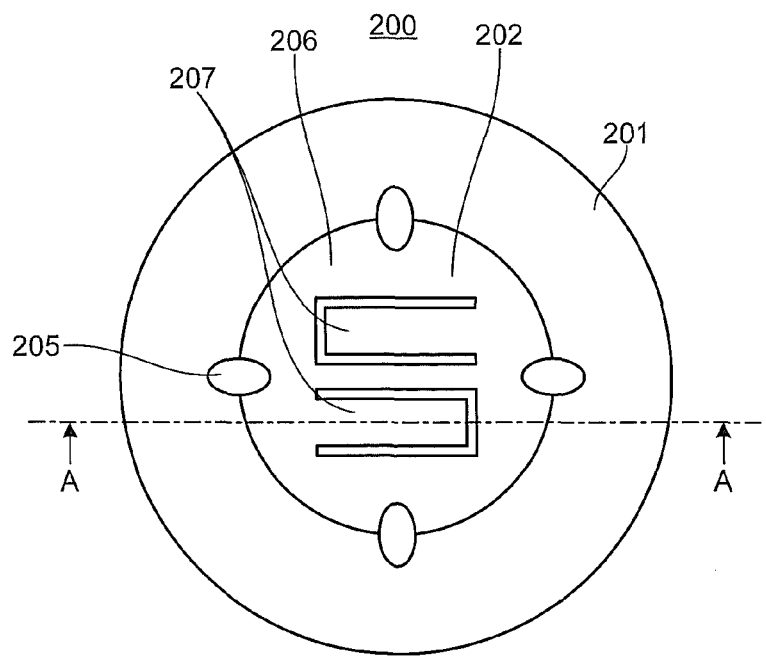
FIG. 8A is a top view illustrating a short-circuit prevention member illustrated in FIG. 7.
Figure 8B:
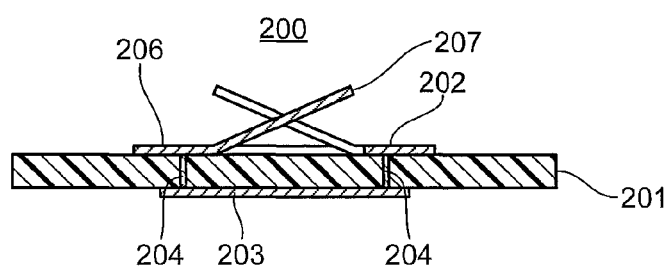
FIG. 8B is a sectional view taken along a line A-A in FIG. 8A.
Figure 8C:
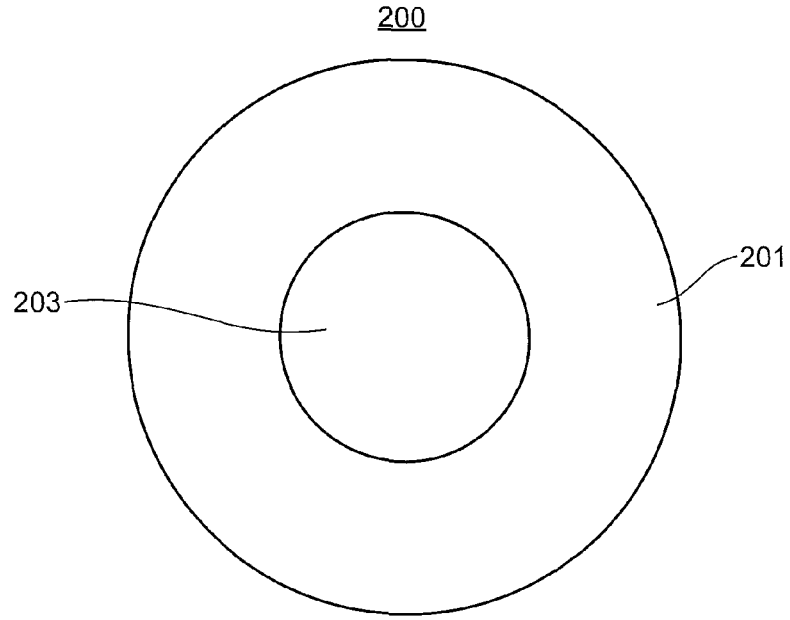
FIG. 8C is a bottom view illustrating a short-circuit prevention member illustrated in FIG. 7.

FIG. 8A is a top view illustrating the short-circuit prevention member 200, FIG. 8B is a sectional view taken along a line A-A in FIG. 8A, and FIG. 8C is a bottom view illustrating the short-circuit prevention member 200. As illustrated in FIGS. 8A to 8C, the short-circuit prevention member 200 includes an insulating substrate 201, a contact spring member 202 provided on one surface of the insulating substrate 201, and an electrode pad 203 provided on the other surface of the insulating substrate 201. The contact spring member 202 and the electrode pad 203 are electrically connected to each other by a through-hole 204 formed in the insulating substrate 201.

The insulating substrate 201 is made of an insulating material such as a flexible substrate, and has a disk shape whose outer diameter is smaller than the inner diameter of the casing 10 (the case portion 102) and preferably larger than the outer diameter of the batteries 141 and 142.

The contact spring member 202 is a metal member with a disk shape whose outer diameter is smaller than the insulating substrate 201, and it is mounted on the insulating substrate 201 by using solder 205. The contact spring member 202 includes a plane portion 206, and one or more (two in FIG. 8A) spring portions 207 that stand from the plane portion 206 in oblique direction to be elastically deformable. In the second embodiment, each spring portion 207 includes a tongue-like region that is formed by cutting a part of the plane metal member and that is partly connected to the plane portion 206. Each spring portion 207 is formed by rising the tongue-like region from the plane portion 206 toward one side with respect to the major surface of the plane portion 206. Reaction force of the spring portion 207 is set such that the contact resistance with the positive-electrode surface 1b becomes smaller than a predetermined value in total. The contact spring member 202 described above is arranged on the side close to the positive-electrode surface 1b of the battery 141, and is in contact with the positive-electrode surface 1b to be electrically connected to the same.

On the other hand, the electrode pad 203 is a disk-like metal member having an outer diameter smaller than the diameter of the negative electrode 1c. The electrode pad 203 is in contact with the negative electrode 1c of the battery 142 to be electrically connected to the same.

The method of manufacturing the capsule medical device 2 is the same as the method described in the first embodiment with reference to FIGS. 5A to 5F.

According to the second embodiment described above, the short-circuit prevention member 200 is arranged between the battery 141 and the battery 142, whereby the short-circuit on the negative-electrode surface 1a of the battery 142 can be prevented, while securing the electrical connection between the battery 141 and the battery 142. In the second embodiment, the contact spring member 202 having spring property is provided to the short-circuit prevention member 200, whereby the contact point between the batteries 141 and 142 can surely be formed independently of the variation in the thickness of the insulating substrate 201.

Modification 2-1

Subsequently, Modification 2-1 of the second embodiment will be described.

In the short-circuit prevention member 200, the outer diameters of the contact spring member 202 and the electrode pad 203 provided on both surfaces of the insulating substrate 201 may be set to be smaller than the diameter of the negative electrode 1c. In this case, the conductive contact spring member and the electrode pad are not brought into contact with the peripheral edge positive-electrode portion 1e, even if either one of the contact spring member 202 and the electrode pad 203 faces the battery 142. Therefore, it is unnecessary to consider the front and back of the short-circuit prevention member 200 upon assembling the capsule medical device 2, whereby the assembling process can be simplified.

Third Embodiment

Subsequently, a third embodiment of the present invention will be described.

Figure 9:
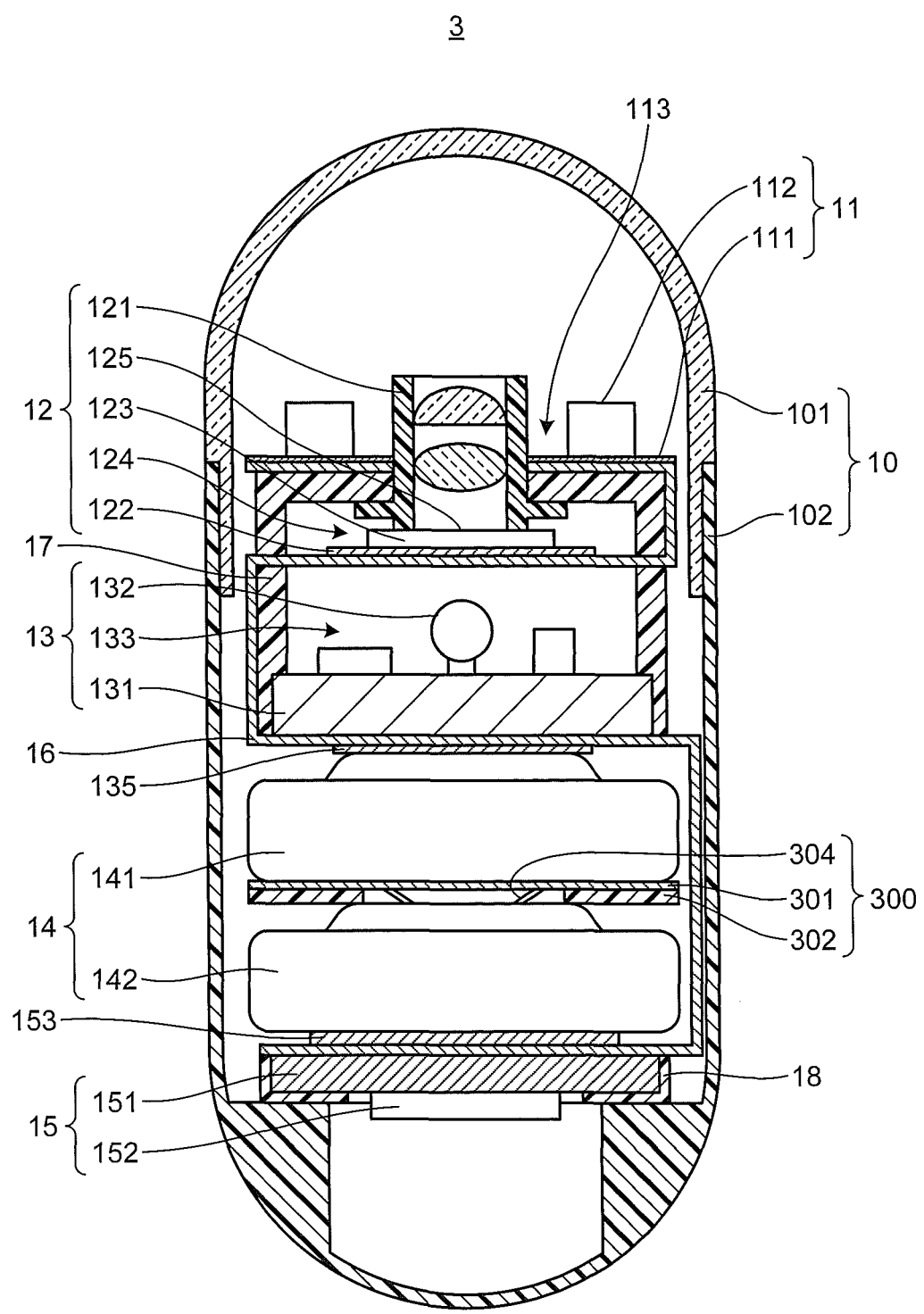
FIG. 9 is a sectional view illustrating an example of a configuration of a capsule medical device according to a third embodiment of the present invention.

FIG. 9 is a sectional view illustrating a configuration of a capsule medical device according to the third embodiment of the present invention. As illustrated in FIG. 9, a capsule medical device 3 according to the third embodiment includes a short-circuit prevention member 300 instead of the short-circuit prevention member 200 illustrated in FIG. 7. The configuration of the capsule medical device 3 except for the short-circuit prevention member 300 is the same as that illustrated in FIG. 7.

The short-circuit prevention member 300 is arranged between the battery 141 and the battery 142. It electrically connects the battery 141 and the battery 142, and prevents a short-circuit between the negative electrode 1c and the peripheral edge positive-electrode portion 1e on the negative-electrode surface 1a of the battery 142.

Figure 10A:
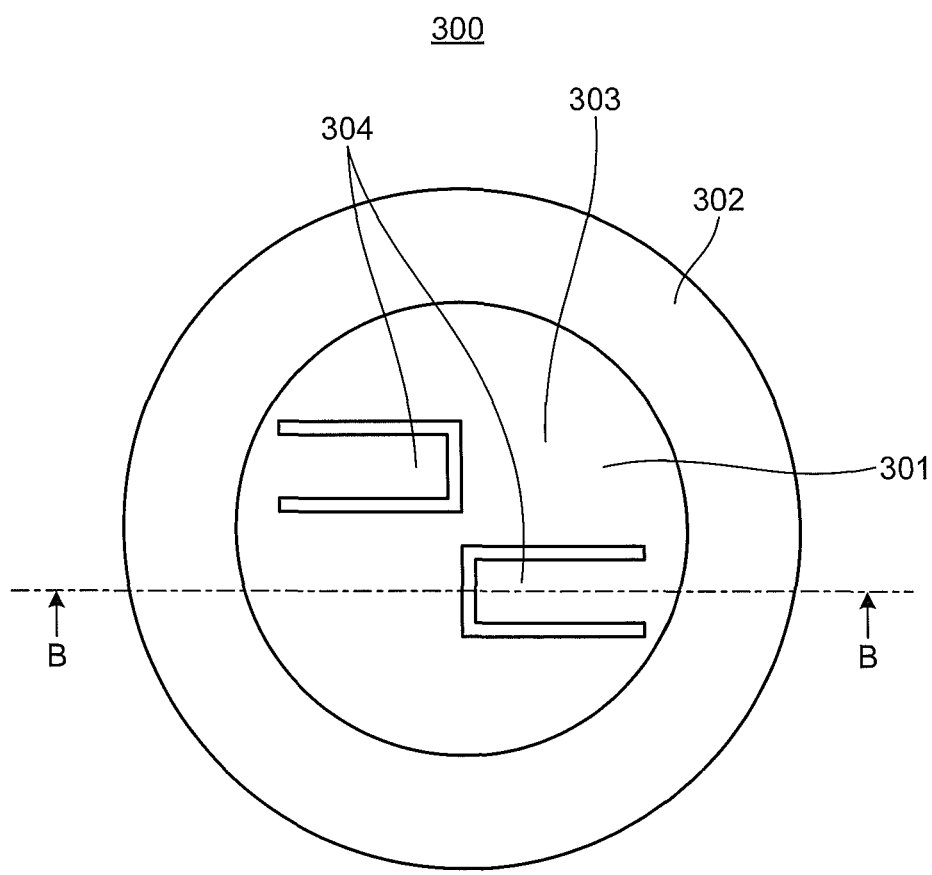
FIG. 10A is a top view illustrating a short-circuit prevention member illustrated in FIG. 9.
Figure 10B:
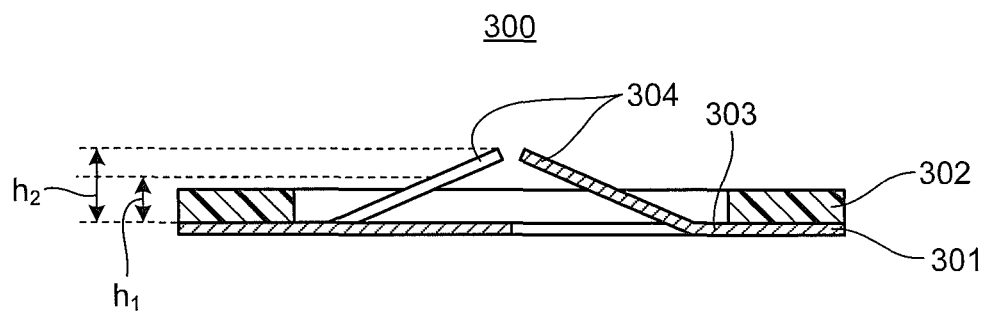
FIG. 10B is a sectional view taken along a line B-B in FIG. 10A.

FIG. 10A is a top view illustrating the short-circuit prevention member 300, and FIG. 10B is a sectional view taken along a line B-B in FIG. 10A. As illustrated in FIGS. 10A and 10B, the short-circuit prevention member 300 includes a contact spring member 301 having a disk-like shape, and an annular insulating member 302 provided on the peripheral edge of one surface of the contact spring member 301.

The contact spring member 301 is a metal member whose diameter is smaller than the inner diameter of the casing 10 (the case portion 102) and larger than the inner diameter of the peripheral edge positive-electrode portion 1e (see FIG. 3A). The contact spring member 301 includes a plane portion 303, and one or more (two in FIG. 10A) spring portions 304 that stand from the plane portion 303 in oblique direction to be elastically deformable. In the third embodiment, each spring portion 304 includes a tongue-like region that is formed by cutting a part of the plane metal member and that is partly connected to the plane portion 303. Each spring portion 301 is formed by rising the tongue-like region from the plane portion 303 toward one side with respect to the major surface of the plane portion 303.

The contact spring member 301 described above is arranged such that the side where the spring portion 304 stands faces the negative electrode 1c of the battery 142. Therefore, the spring portion 304 is positioned such that the distal end region serving as the contact point to the negative electrode 1c is put inside the diameter of the negative electrode 1c. Reaction force of the spring portion 304 is set such that the contact resistance with the battery 142 becomes smaller than a predetermined value in total.

The insulating member 302 is bonded to the peripheral edge of the plane portion 303 on the side where the spring portion 304 stands with an adhesive agent. The outer diameter of the insulating member 302 is smaller than the inner diameter of the case portion 102, and larger than the outer diameter of the batteries 141 and 142. On the other hand, the inner diameter of the insulating member 302 is smaller than the inner diameter of the peripheral edge positive-electrode portion 1e (see FIG. 3A), and has a size by which the spring portion 304 can be exposed. In the third embodiment, the outer diameter of the insulating member 302 and the outer diameter of the contact spring member 301 are set to be the same.

The thickness of the insulating member 302 is preferably set to be not more than a lower limit (i.e., height $h_2$) of a moving range (height $h_1$ to $h_2$) of the spring portion 304. The height $h_1$ is the height of the spring portion 304 measured from the plane portion 303 before the short-circuit prevention member 300 is mounted to the capsule medical device 3, and the height $h_2$ is the height of the spring portion 304 measured from the plane portion 303 after the short-circuit prevention member 300 is mounted to the capsule medical device 3.

The height $h_1$ from the plane portion 303 can be preliminarily set in order to prevent the spring portion 304 from being displaced in an amount not less than a certain amount, for preventing the plastic deformation of the spring portion 304.

The insulating member 302 described above is made of an insulating material such as resin or rubber. Preferably, the insulating member is made of a material having excellent elasticity, such as a silicon rubber, for easily stopping the movement of the battery 142 by friction force through an intimate contact with the battery 142 when it is in contact with the battery 142.

The short-circuit prevention member 300 is arranged in the capsule medical device 3 in a state in which the spring portion 304 is brought into contact with the negative electrode 1c of the battery 142, and the surface of the contact spring member 301 on the side reverse to the side where the spring portion 304 stands is brought into contact with the positive-electrode surface 1b of the battery 141. The method of manufacturing the capsule medical device 3 is the same as the method described in the first embodiment.

According to the third embodiment described above, the short-circuit on the negative-electrode surface 1a of the battery 142 can be prevented, while securing the electrical connection between the battery 141 and the battery 142. Since the short-circuit prevention member 300 has a simple structure in which the insulating member 302 is bonded to the contact spring member 301 with the adhesive agent, a soldering process is unnecessary, whereby the assembling property of the short-circuit prevention member 300 can be enhanced.

In the third embodiment, the insulating member 302 may also be made of a seal-type adhesive member or a coating material having adhesive property on one surface. In this case, it is unnecessary to prepare an adhesive agent in a process of providing the insulating member 302 to the contact spring member 301, whereby the process can further be simplified.

A process of enhancing a friction coefficient on the contact surface with the positive-electrode surface 1b may be performed to the contact spring member 301 for preventing the positional deviation between the batteries 141 and 142.

Fourth Embodiment

Subsequently, a fourth embodiment of the present invention will be described.

Figure 11A:
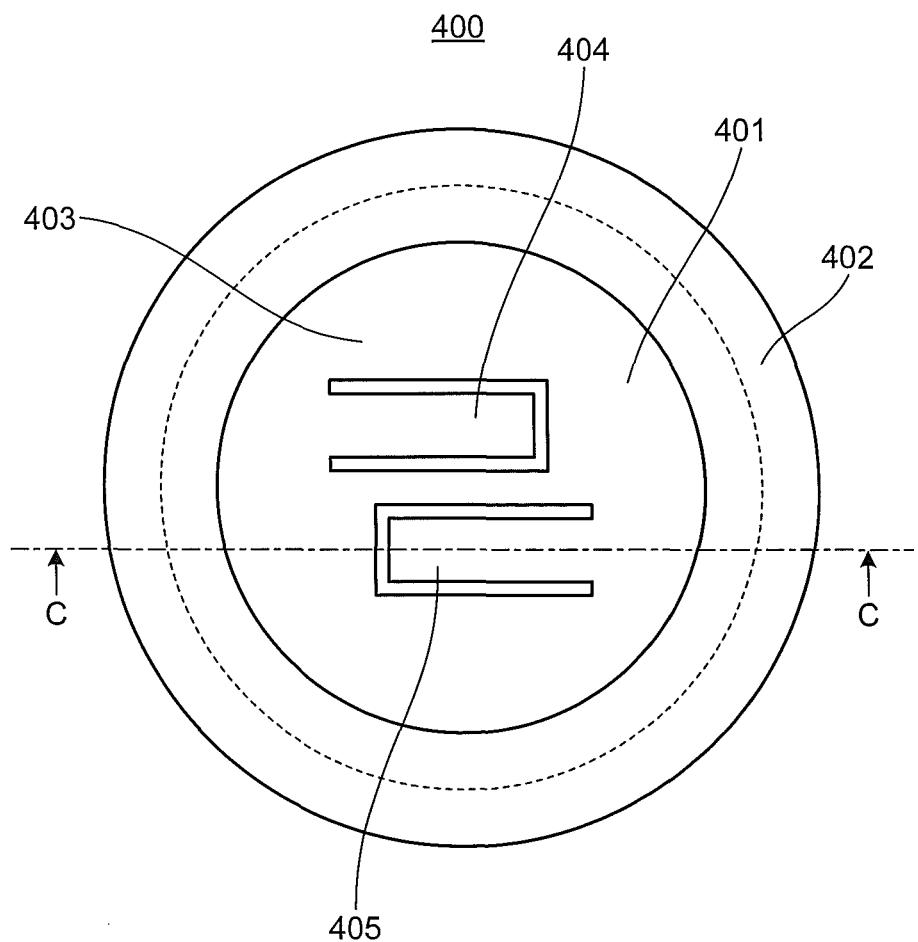
FIG. 11A is a top view illustrating a configuration of a short-circuit prevention member provided in a capsule medical device according to a fourth embodiment of the present invention.
Figure 11B:
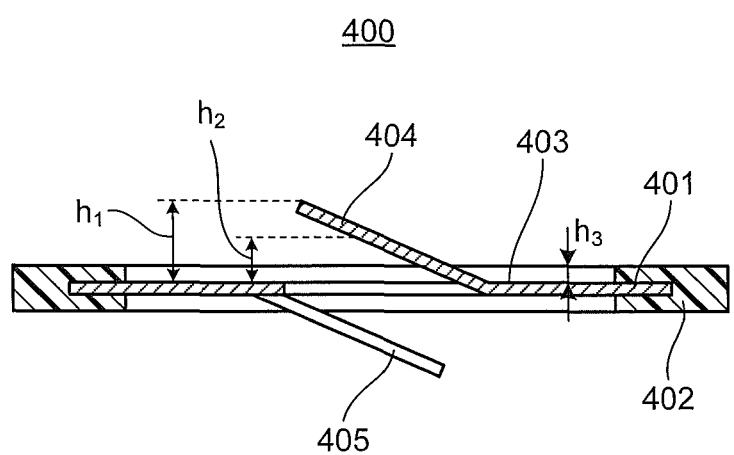
FIG. 11B is a sectional view taken along a line C-C in FIG. 11A.

A capsule medical device according to the fourth embodiment includes a short-circuit prevention member 400 illustrated in FIGS. 11A and 11B instead of the short-circuit prevention member 300 illustrated in FIG. 9. The configuration of the capsule medical device according to the fourth embodiment except for the short-circuit prevention member 400 is the same as that illustrated in FIG. 9.

FIG. 11A is a top view illustrating the short-circuit prevention member 400, and FIG. 11B is a sectional view taken along a line C-C in FIG. 11A. As illustrated in FIGS. 11A and 11B, the short-circuit prevention member 400 includes a contact spring member 401 having a disk-like shape, and an annular insulating member 402 provided on the peripheral edge of the contact spring member 401.

The contact spring member 401 is a metal member whose diameter is smaller than the inner diameter of the casing 10 (the case portion 102) and larger than the inner diameter of the peripheral edge positive-electrode portion 1e (see FIG. 3A). The contact spring member 401 includes a plane portion 403, and two spring portions 404 and 405 that stand toward both sides (upward and downward in the figure) in oblique directions from the plane portion 403 and that are elastically deformable. In the fourth embodiment, each of the spring portions 404 and 405 includes a tongue-like region that is formed by cutting a part of the plane metal member and that is partly connected to the plane portion 403. Each spring portion is formed by rising the tongue-like region from the plane portion 403 toward both sides with respect to the major surface of the plane portion 403. The number of the spring portions may be two or more in total, and it is only necessary that at least one spring portion stands on each side of the plane portion 403. Reaction force of the spring portions 404 and 405 is set such that the contact resistance with the batteries 141 and 142 becomes smaller than a predetermined value in total.

The outer diameter of the insulating member 402 is smaller than the inner diameter of the case portion 102, and larger than the outer diameter of the batteries 141 and 142. On the other hand, the inner diameter of the insulating member 402 is smaller than the peripheral edge positive-electrode portion 1e (see FIG. 3A), and has a size by which the spring portions 404 and 405 can be exposed. The thickness of the insulating member 402 is preferably set such that a height $h_3$ from the plane portion 403 to the top surface of the insulating member 402 is not more than a lower limit (i.e., height $h_2$) of a moving range (height $h_1$ to $h_2$) of the spring portions 404 and 405.

The insulating member 402 described above is made of an insulating material such as resin or rubber. Preferably, the insulating member is made of a material having excellent elasticity, such as a silicon rubber, for easily stopping the movement of the batteries 141 and 142 by friction force through an intimate contact with the batteries 141 and 142 when it is arranged between the batteries 141 and 142. A process for enhancing a friction coefficient on the contact surface with the batteries 141 and 142 may be performed to the insulating member 402. With this process, the positional deviation of the batteries 141 and 142 can further be prevented.

The insulating member 402 may be formed integral with the contact spring member 401 by an insert molding. Alternatively, the insulating member 402 may be formed by bonding two annular members having insulating property to the peripheral edge of the plane portion 403 from both sides.

According to the fourth embodiment described above, the short-circuit on the negative-electrode surface 1a of the battery 142 can be prevented, while securing the electrical connection between the battery 141 and the battery 142. Particularly, in the fourth embodiment, the contact point to the positive-electrode surface 1b of the battery 141 and the negative electrode 1c of the battery 142 are formed by the spring portions 404 and 405, whereby the electrical connection between the batteries 141 and 142 can surely be secured. In addition, in the fourth embodiment, since the contact spring member 401 and the insulating member 402 can integrally be formed by the insert molding, the short-circuit prevention member 400 can be mass-produced, the manufacturing process becomes more efficient, and the manufacturing cost can be reduced.

Modification 4-1

Subsequently, Modification 4-1 of the fourth embodiment will be described.

Figure 12:
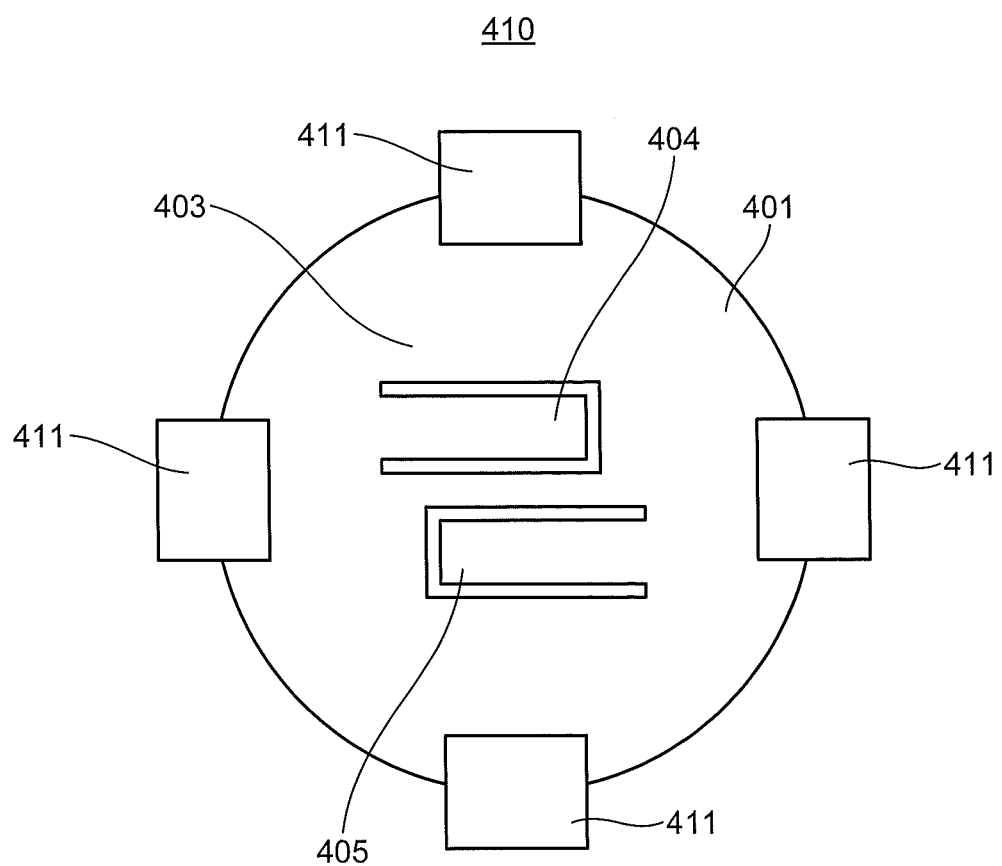
FIG. 12 is a top view illustrating a configuration of a short-circuit prevention member according to Modification 4-1.

FIG. 12 is a top view illustrating a configuration of a short-circuit prevention member 410 according to Modification 4-1. The shape of the insulating member on the peripheral edge of the contact spring member 401 is not limited to the annular shape illustrated in FIG. 11A. For example, as illustrated in FIG. 12, the contact spring member 401 may be held by plural insulating member pieces 411. In this case, it is only necessary that three or more insulating member pieces 411 are provided.

Fifth Embodiment

Subsequently, a fifth embodiment of the present invention will be described.

Figure 13:
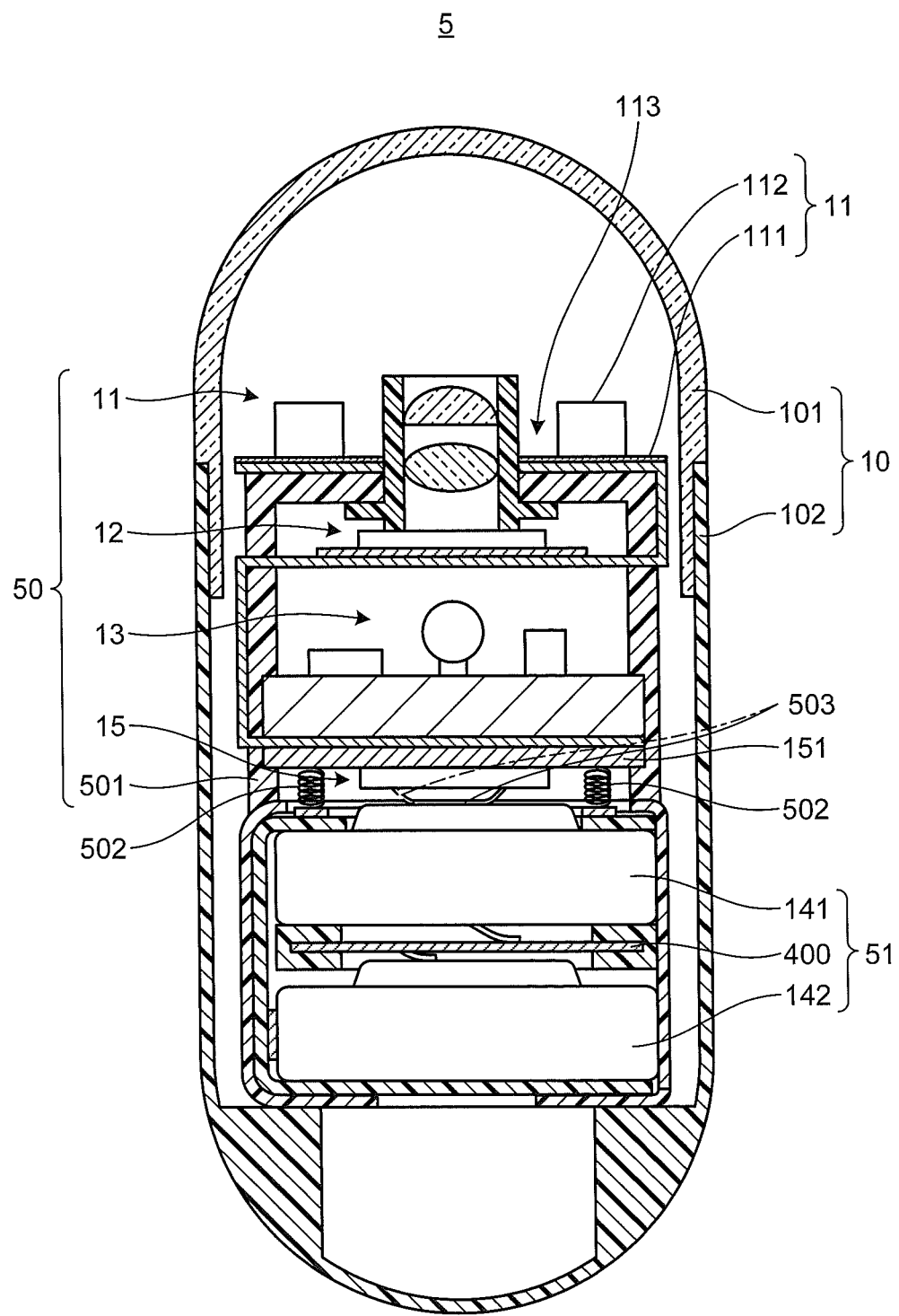
FIG. 13 is a sectional view illustrating an example of a configuration of a capsule medical device according to a fifth embodiment of the present invention.

FIG. 13 is a sectional view illustrating a configuration of a capsule medical device according to the fifth embodiment. As illustrated in FIG. 13, a capsule medical device 5 according to the fifth embodiment includes a function execution unit 50 including an illumination unit 11, an imaging unit 12, a control unit 13, and a wireless communication unit 15 as a unit by a spacer 501, and a battery unit 51 including batteries 141 and 142 as a unit. A positive-electrode contact 502 and a negative-electrode contact 503 that are electrically connected to the battery unit 51 are formed on a wireless substrate 151 arranged on an end of the function execution unit 50. The detailed configuration of each function execution section in the function execution unit 50 is the same as that described in the first embodiment.

Figure 14A:
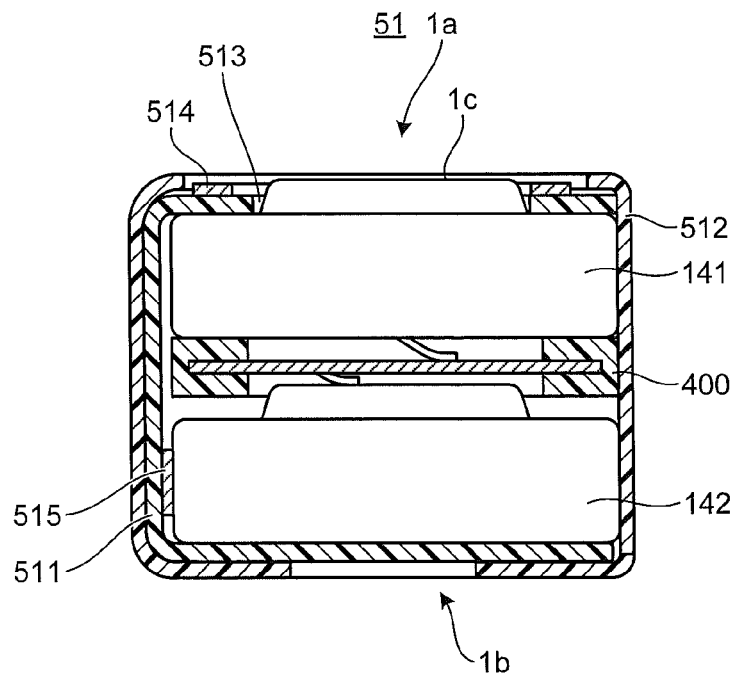
FIG. 14A is a sectional view of a battery unit illustrated in FIG. 13.
Figure 14B:
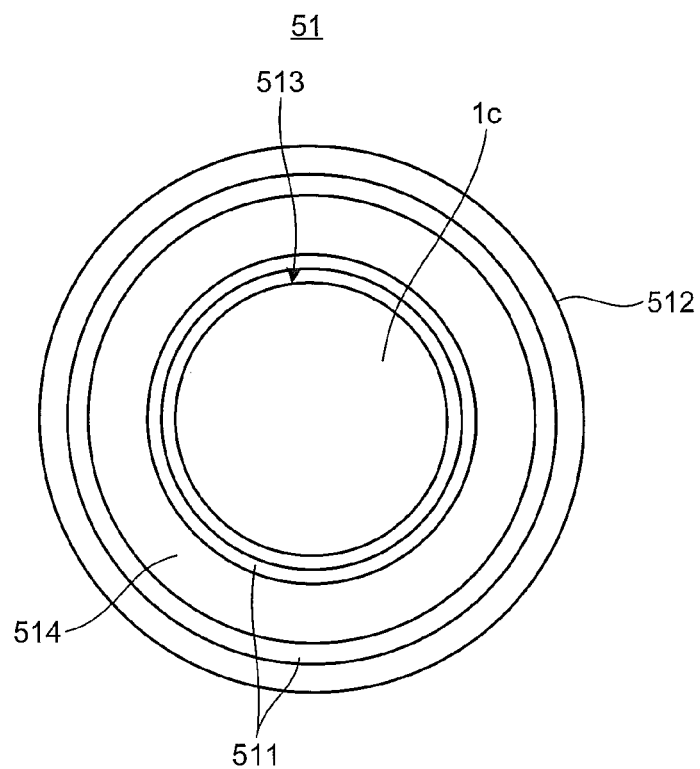
FIG. 14B is a top view of the battery unit illustrated in FIG. 13.

FIG. 14A is a sectional view illustrating the battery unit 51, and FIG. 14B is a top view illustrating the battery unit 51. As illustrated in FIG. 14A, the battery unit 51 includes batteries 141 and 142 coaxially superimposed, a short-circuit prevention member 400 arranged between the batteries 141 and 142, a flexible substrate 511 that extends from the negative-electrode surface 1a of the battery 141 to the positive-electrode surface 1b of the battery 142, and a fastening member 512 that combines these components.

As illustrated in FIG. 14B, the end of the flexible substrate 511 near the battery 141 has a circular shape almost equal to the batteries 141 and 142, and an aperture 513 through which the negative electrode 1c is inserted is formed on its central part. The inner diameter of the aperture 513 is smaller than the peripheral edge positive-electrode portion 1e (see FIG. 3A). With this structure, the surface of the peripheral edge positive-electrode portion 1e is covered by the flexible substrate 511 on the negative-electrode surface 1a of the battery 141.

An annular electrode pad 514 is provided on the top surface of the flexible substrate 511 around the aperture 513. The electrode pad 514 is a contact member with the positive-electrode contact 502 of the function execution unit 50. Since the electrode pad 514 is formed to have an annular shape, the positioning between the battery unit 51 and the function execution unit 50 in the circumferential direction is unnecessary upon the assembly.

An electrode pad 515 is provided on the surface of the flexible substrate 511 near the side face of the battery 142. The electrode pad 515 is connected to the electrode pad 514 via a circuit unit mounted on the flexible substrate 511. With this structure, the positive electrode of the battery 142 is extended around the negative-electrode surface 1a of the battery 141. A spring contact member that is in contact with the side face of the battery 142 to bias the battery 142 in the diameter direction may be provided instead of the electrode pad 515.

A fastening member 512 is a heat shrinkable tube, for example. It externally encloses and holds the batteries 141 and 142, the short-circuit prevention member 400 arranged between the batteries, and the flexible substrate 511, and presses the flexible substrate 511 against the battery 142 to bring the electrode pad 515 into contact with the side face of the battery 142.

Subsequently, a method of assembling the capsule medical device 5 will be described.

Firstly, as illustrated in FIG. 15A, the battery unit 51 is inserted into the case portion 102 with the negative-electrode surface 1a facing the aperture of the case portion 102.

Then, as illustrated in FIG. 15B, the function execution unit 50 is inserted into the case portion 102 from the side of the positive-electrode contact 502 and the negative-electrode contact 503. With this process, the positive-electrode contact 502 is electrically connected to the positive electrode of the battery 142 via the electrode pad 514, the circuit unit mounted on the flexible substrate 511, and the electrode pad 515 (see FIG. 14A), while the negative-electrode contact 503 is electrically connected to the negative electrode 1c of the battery 141.

As illustrated in FIG. 15C, the dome portion 101 is put on the case portion 102, and they are bonded by using an adhesive to seal the casing 10. Thus, the capsule medical device 5 is completed.

As described above, according to the fifth embodiment, each of the function execution sections and the batteries 141 and 142 are formed as a unit, and the positive electrode and the negative electrode are arranged on the top surface of the battery unit 51, whereby the capsule medical device 5 can be assembled only by putting the battery unit 51 and the function execution unit 50 into the case portion 102. Accordingly, the procedure of the assembly of the capsule medical device 5 can be simplified, and the time taken for the assembling process can be reduced.

In the fifth embodiment, the short-circuit prevention member 400 is arranged between the batteries 141 and 142. However, instead of this configuration, the short-circuit prevention members 143, 200, or 300 according to the first to third embodiments or the short-circuit prevention member 410 according to Modification 4-1 may be arranged.

Sixth Embodiment

Subsequently, a sixth embodiment of the present invention will be described.

Figure 16:
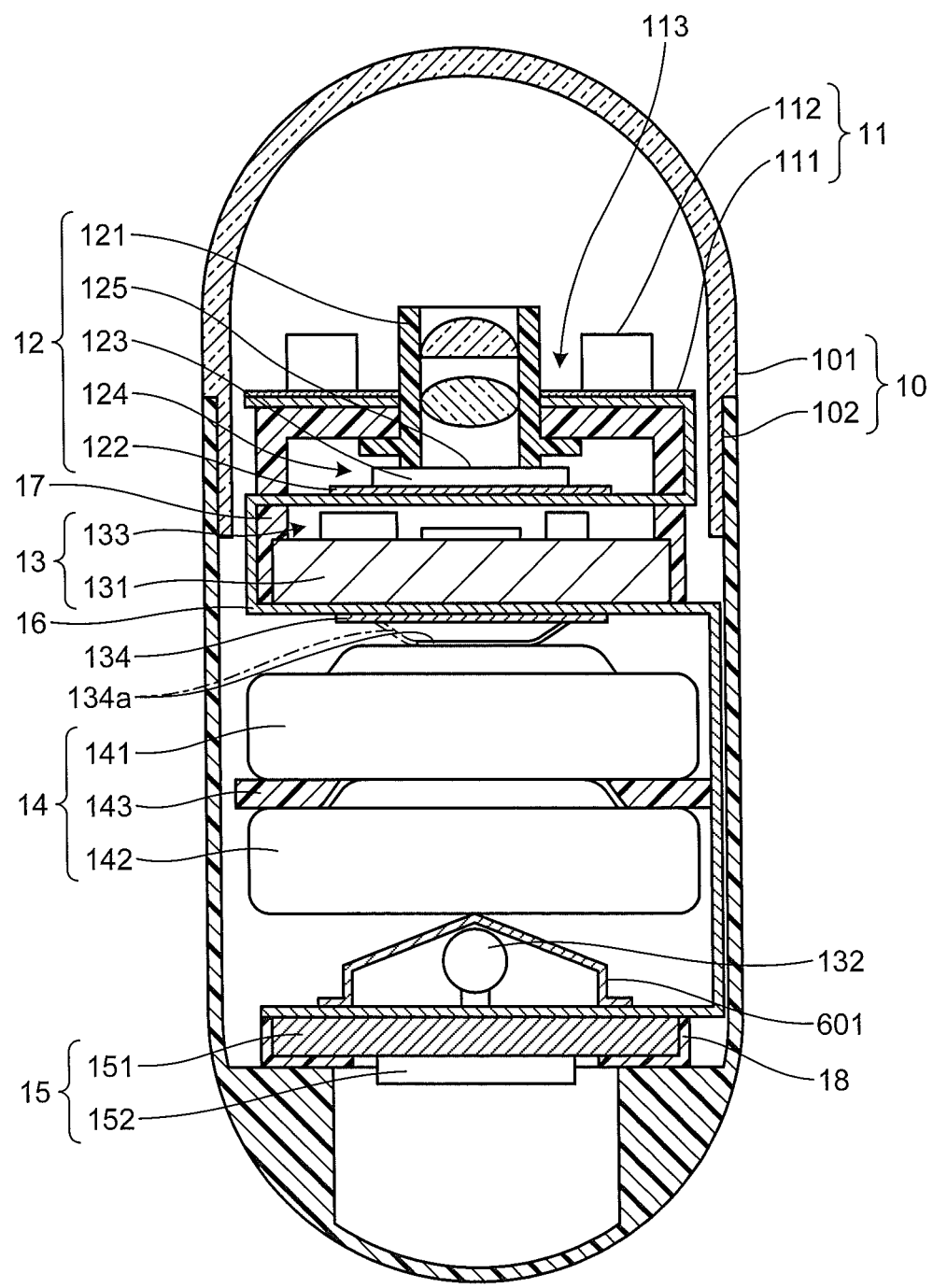
FIG. 16 is a sectional view illustrating an example of a configuration of a capsule medical device according to a sixth embodiment of the present invention.

FIG. 16 is a sectional view illustrating a configuration of a capsule medical device according to the sixth embodiment. As illustrated in FIG. 16, a capsule medical device 6 according to the sixth embodiment has a configuration in which a lead switch 132 is provided on a wireless communication unit 15 in the capsule medical device 1 illustrated in FIG. 1.

If a battery having a ferromagnetic body inside is present in the vicinity of the wireless communication unit 15, a wireless communication function might be deteriorated upon transmitting data acquired in the capsule medical device 6 to the outside of the subject. In such case, it is preferable that the wireless communication unit 15 and the battery or other components are arranged with a space. However, such arrangement might generate a dead space, and prevent the efficient arrangement of the components housed in the casing 10.

In the sixth embodiment, the lead switch 132 that occupies a space on the control unit 13 is moved on the wireless communication unit 15. According to this structure, the control unit 13 can be downsized, and the battery unit 14 is moved close to the control unit 13. A contact member 601 electrically connected to the lead switch 132 and the battery unit 14 is provided in a space (back side of the wireless substrate 151) generated because of the movement of the battery unit 14.

According to the sixth embodiment described above, the wireless communication unit 15 and the batteries 141 and 142 are separated, whereby the deterioration in the wireless communication function can be prevented, and the space in the casing 10 can effectively be utilized.

Seventh Embodiment

Subsequently, a seventh embodiment of the present invention will be described.

Figure 17A:
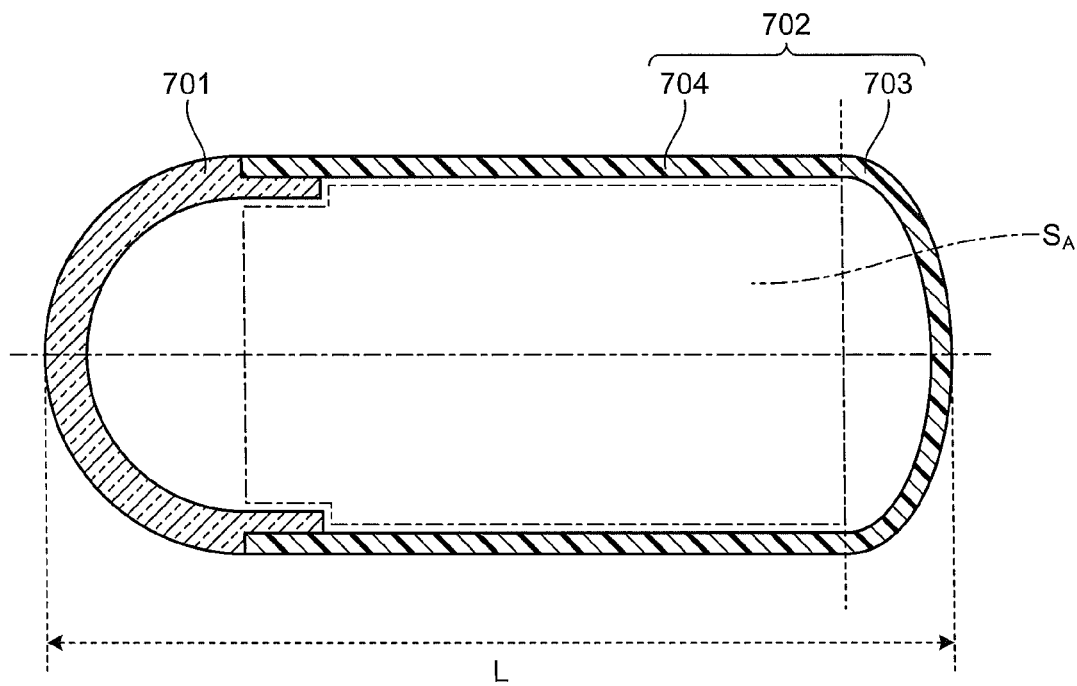
FIG. 17A is a sectional view illustrating a shape of a casing of a capsule medical device according to a seventh embodiment of the present invention.
Figure 17B:
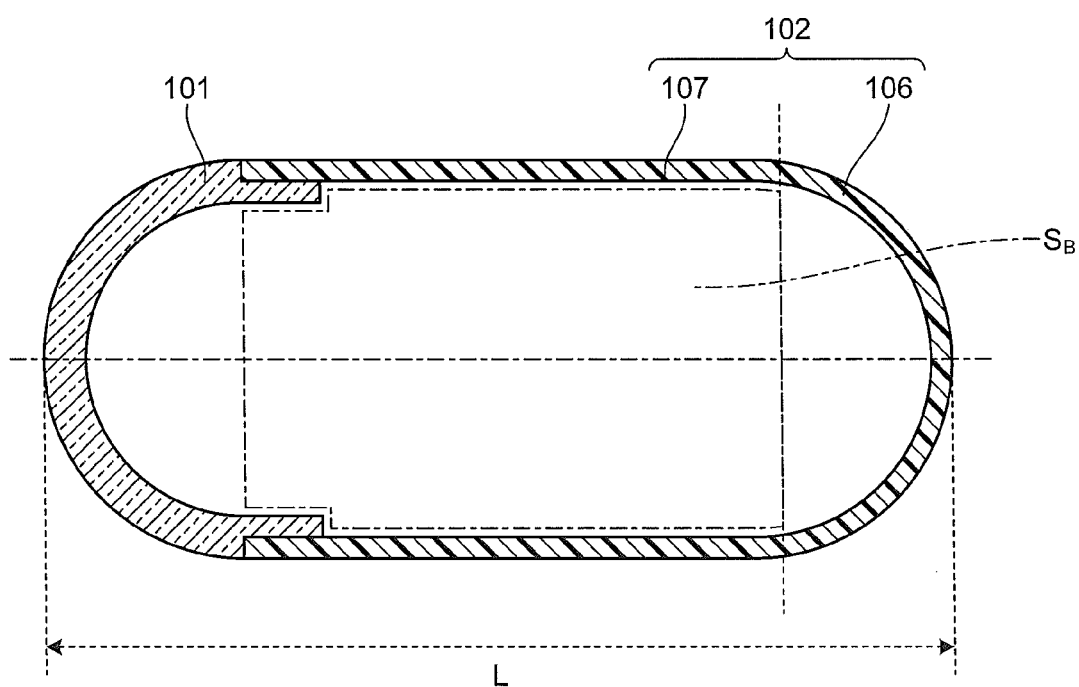
FIG. 17B is a sectional view illustrating a shape of a general casing of a capsule medical device.

FIG. 17A is a sectional view illustrating a casing of a capsule medical device according to the seventh embodiment, and FIG. 17B is a sectional view illustrating a general casing of a capsule medical device. As illustrated in FIG. 17A, a casing 70 of the capsule medical device according to the seventh embodiment includes a dome portion 701 having a hemispherical shape and a bottomed case portion 702 having a cylindrical portion. The shape of the dome portion 701 is the same as the dome portion 101 in a general casing 10.

As illustrated in FIG. 17B, the bottom (the case hemispherical portion 106) of the case portion 102 has a hemispherical shape in the general casing 10. Therefore, the internal space is narrowed toward the end of the case portion 102, and it is difficult to efficiently arrange the components in the casing 10. For example, when the component having the outer diameter almost equal to the inner diameter of the case portion 102 is housed, almost all internal space of the case hemispherical portion 106 becomes a dead space. In this case, the substantial arrangement space $S_B$ in the casing 10 is up to the end of the case cylindrical portion 107.

On the other hand, a bottom 703 of the case portion 702 has a shape with a cross-section that is a semi-ellipse having a long axis almost equal to the diameter of a case cylindrical portion 704. Therefore, when the length L from the distal end of the dome portion 701 to the rear end of the case portion 702 is equal to the length of the general casing 10, the length of the case cylindrical portion 704 can be increased. Specifically, the substantial arrangement space $S_A$ for the components to be housed can be increased more than the general casing 10.

As described above, according to the seventh embodiment, the internal space for housing the components to be housed can be increased to reduce the dead space.

According to the first to seventh embodiments and the modifications thereof described above, a short-circuit prevention member that secures the electrical connection among plural batteries and obtains insulation between a first electrode and a portion of a second electrode on a peripheral edge is arranged among the plural batteries, whereby a short-circuit of the battery during the assembly process or during the use of the device can be prevented.

The embodiments and the modifications described above have been presented by way of example only, and are not intended to limit the inventions. In addition, the present invention can generate various inventions by appropriately combining plural constituents described in the embodiments and the modifications. It is obvious that the present invention can be modified in various forms according to a specification, and various embodiments are possible without departing from the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

(Appendix 1)

A capsule medical device including:

a casing having a capsule shape;

a plurality of batteries that feed power supply to various devices provided in the casing, each battery having a first face and a second face opposite to the first face, a first electrode being provided on a central region of the first face to project from the first face, a second electrode being provided over a peripheral edge of the first face through a side face from the second face, and the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein the short-circuit prevention member includes an insulating member having an annular shape, covering the portion of the second electrode, and formed with an aperture from which the first electrode is exposed, an outer diameter of the annular shape is smaller than an inner diameter of the casing, and larger than an outer diameter of the batteries, a diameter of the aperture is larger than a diameter of the first electrode, and smaller than a diameter of the portion of the second electrode, and the insulating member is brought into contact with at least one of the plurality of batteries to stop the movement of the at least one battery by friction force.

(Appendix 2)

A capsule medical device including:

a casing having a capsule shape;

a plurality of batteries that feed power supply to various devices provided in the casing, each battery having a first face and a second face opposite to the first face, a first electrode being provided on a central region of the first face to project from the first face, a second electrode being provided over a peripheral edge of the first face through a side face from the second face, and the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein the first electrode is a negative electrode, and
the second electrode is a positive electrode.

What is claimed is:

1. A capsule medical device comprising:
a casing having a capsule shape;
a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and
a short-circuit prevention member that is arranged among the plurality of batteries to secure an electrical connection among the plurality of batteries and to obtain insulation between the first electrode and a portion of the second electrode on the peripheral edge, wherein
the short-circuit prevention member includes an insulating member having an annular shape, covering the portion of the second electrode, and formed with an aperture from which the first electrode is exposed,
an outer diameter of the annular shape is smaller than an inner diameter of the casing, and larger than an outer diameter of the battery,
a diameter of the aperture is larger than a diameter of the first electrode, and smaller than a diameter of the portion of the second electrode; and
a cross-section of the aperture of the insulating member, the cross-section being orthogonal to the aperture face, has a taper shape.

2. A capsule medical device comprising:
a casing having a capsule shape;
a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and a short-circuit prevention member that is arranged among the plurality of batteries to secure an electrical connection among the plurality of batteries and to obtain insulation between the first electrode and a portion of the second electrode on the peripheral edge, wherein
the short-circuit prevention member includes:
an insulating member having a disk-like shape,
an electrode pad provided on one surface of the insulating member and is in contact with at least a part of the first electrode,
a contact member that is provided on the other surface of the insulating member, and is in contact with the second face, and
a conductive unit that is provided in the insulating member for electrically connecting the electrode pad and the contact member.

3. The capsule medical device according to claim 2, wherein a diameter of the insulating member is smaller than an inner diameter of the casing, and larger than an outer diameter of the battery.

4. The capsule medical device according to claim 2, wherein a diameter of the electrode pad is not more than a diameter of the first electrode.

5. The capsule medical device according to claim 2, wherein the contact member includes a plane portion, and a spring portion standing from the plane portion in an oblique direction.

6. A capsule medical device comprising:
a casing having a capsule shape;
a plurality of batteries that feed power supply to various devices provided in the casing, each battery having a first face, a second face opposite to the first face, a first electrode provided on a central region of the first face to project from the first face and a second electrode provided over a peripheral edge of the first face through a side face from the second face, the first electrode and the second electrode being electrically insulated from each other via a separator; and
a short-circuit prevention member that is arranged among the plurality of batteries to secure an electrical connection among the plurality of batteries and to obtain insulation between the first electrode and a portion of the second electrode on the peripheral edge, wherein
the short-circuit prevention member includes
a contact member including a plane portion, and at least two spring portions standing from the plane portion toward both sides, respectively, in an oblique direction with respect to a major surface of the plane portion,
an insulating member that has an annular shape formed with an aperture on its central part, and that covers a peripheral edge of a major surface on both sides of the plane portion. and
the insulating member is formed by bonding two annular members, having insulating property, on the peripheral edges of the major surfaces on both sides of the plane portion.

* * * * *